US009266816B2

(12) United States Patent
Shrawat et al.

(10) Patent No.: US 9,266,816 B2
(45) Date of Patent: Feb. 23, 2016

(54) FINGOLIMOD POLYMORPHS AND THEIR PROCESSES

(75) Inventors: Vimal Kumar Shrawat, Karnataka (IN); Veereshappa, Karnataka (IN); Vinod Kumar Singh, Karnataka (IN); Prashant Purohit, Karnataka (IN)

(73) Assignee: SHILPA MEDICARE LIMITED, Karnataka (IN)

( * ) Notice: Subject to any disclaimer, the term of this patent is extended or adjusted under 35 U.S.C. 154(b) by 0 days.

(21) Appl. No.: 13/635,207

(22) PCT Filed: Aug. 29, 2011

(86) PCT No.: PCT/IN2011/000586
§ 371 (c)(1),
(2), (4) Date: Sep. 17, 2013

(87) PCT Pub. No.: WO2012/070059
PCT Pub. Date: May 31, 2012

(65) Prior Publication Data
US 2013/0281739 A1      Oct. 24, 2013

(30) Foreign Application Priority Data
Nov. 25, 2010   (IN) .......................... 3563/CHE/2010

(51) Int. Cl.
| C07C 213/10 | (2006.01) |
| C07C 215/10 | (2006.01) |
| C07C 215/28 | (2006.01) |

(52) U.S. Cl.
CPC ............. *C07C 213/10* (2013.01); *C07C 215/28* (2013.01); *C07B 2200/13* (2013.01)

(58) Field of Classification Search
None
See application file for complete search history.

(56) References Cited

U.S. PATENT DOCUMENTS

| 5,604,229 A | 2/1997 | Fujita et al. |
| 5,719,176 A | 2/1998 | Fujita et al. |
| 5,952,316 A | 9/1999 | Fujita et al. |
| 6,476,004 B1 | 11/2002 | Sakai et al. |
| 2006/0275357 A1 | 12/2006 | Oomura et al. |
| 2008/0311188 A1 | 12/2008 | Oomura et al. |
| 2009/0203798 A1 | 8/2009 | Oomura et al. |
| 2011/0105620 A1 | 5/2011 | Oomura et al. |

(Continued)

FOREIGN PATENT DOCUMENTS

| EP | 0627406 B1 | 10/1998 |
| WO | WO2004089341 A | 10/2004 |
| WO | WO2010055028 A2 | 5/2010 |

OTHER PUBLICATIONS

Durand et al.,"A new Efficient Synthesis of the Immunosuppressive Agent FTY-720", Synthesis 2000, No. 4, 505-506.

(Continued)

*Primary Examiner* — Clinton Brooks

(57) ABSTRACT

The present invention provides crystalline polymorphic forms of Fingolimod HCl (I) and processes for preparation thereof.
The application provides processes for preparation of crystalline polymorphic forms-α, β and μ substantially free from process related impurities. The crystalline polymorphic forms of Fingolimod HCl (I) obtained by the processes according to the present invention having an XRDP pattern as per FIGS. 1, 3 and 5, which are useful as active pharmaceutical ingredient in pharmaceutical compositions for the treatment or prevention of autoimmune related disorder including multiple sclerosis.

6 Claims, 5 Drawing Sheets

(56) References Cited

U.S. PATENT DOCUMENTS

2011/0229501 A1 9/2011 Jordine et al.
2012/0184617 A1 7/2012 Gidwani et al.

OTHER PUBLICATIONS

Kiuchi M et al. Synthesis and immunosuppressive Activity of 2-Substituted 2 Aminopropane-1,3-diolsand 2-Aminoethanols 2000 J of Medicinal Chemistry, 2000, 43 (15), pp. 2946-2961.

FINGOLIMOD POLYMORPHS AND THEIR PROCESSES

FIELD OF THE INVENTION

Particular aspects of the present application relates to the crystalline polymorphic forms α, β and μ of Fingolimod HCl (I) and processes for preparation thereof.

BACKGROUND OF THE INVENTION

Fingolimod hydrochloride has the IUPAC name as 2-amino-2-[2-(4-octylphenyl)ethyl]propane-1,3-diol hydrochloride and have the following structure—

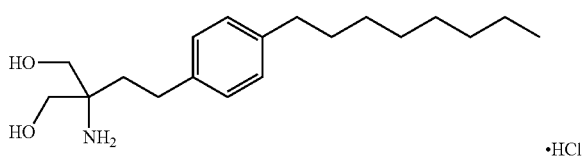

(I)

It is a structural analogue of sphingosine (II) which gets phosphorylated by sphingosine kinases

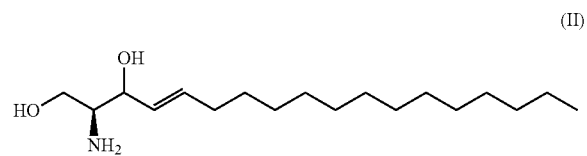 [SMILES: CCCCCCCCCCCCC/C=C/C(O)[C@@H](N)CO]

(II)

in the cell (specifically sphingosine kinase 2).

Fingolimod being a sphingosine 1-phosphate receptor (S1P-R) modulator, it binds to the S1P receptor on circulating lymphocytes, sequestering them in lymph nodes away from the CNS. It appears to be the first oral S1P-R modulator to be developed, which appears to reduce the number of inflammatory T cells in the circulation and CNS and in doing so, it reduces their potential to damage nerve cells.

U.S. Pat. No. 5,604,229 is the first disclosure of the Fingolimod and other related compounds. It has been found to be useful in the treatment or prevention of various autoimmune conditions, including multiple sclerosis.

Mutz et al in WO2010055028A2 reported various polymorphic forms of Fingolimod hydrochloride designated as Form-I (at room temperature), Form-II (however at a transition temperature of approximately 40° C.) and Form-III (however at a transition temperature of approximately 66° C.). Further, the patent application also mentions that approximately 107° C., Fingolimod hydrochloride forms a phase with lower crystalline order. However, other than thermal transition based forms, no exact crystalline form have been reported in the literature.

In view of the existence of few known thermal transition based polymorphic forms of Fingolimod hydrochloride, there stills appears to be a need of novel crystalline forms, which are not only stable as well as convenient to scale up but also their processes provides improved yields & quality.

SUMMARY OF THE INVENTION

Particular aspects of the present application relates to the crystalline polymorphic forms α, β and μ of Fingolimod HCl (I) and processes for preparation thereof.

The application relates to processes for preparation of crystalline polymorphic forms-α, β and μ substantially free from process related impurities. The crystalline polymorphic forms of Fingolimod HCl (I) obtained by the processes according to the present invention are useful as active pharmaceutical ingredient in pharmaceutical compositions for the treatment or prevention of autoimmune related disorder including multiple sclerosis.

Different aspects of the present application are summarized herein below individually.

In one aspect of the present application, the present invention provides Fingolimod hydrochloride crystalline Form-α characterized by X-ray powder diffraction pattern comprising at least 5 characteristic 2θ° peaks selected from the XRPD peak set of 10.51, 15.20, 19.27, 21.77, 23.12, 24.91, 26.14, 26.46, 29.03, 33.47 and 35.46±0.1 2θ°. The said crystalline Form-α is further characterized by DSC isotherm comprising at least three endothermic peaks ranging between—
  a. Peak-1—Between 40 to 43° C.
  b. Peak-2—Between 65 to 68° C.
  c. Peak-3—Between 105 to 110° C.
  d. Peak-4—Between 270 to 280° C.

In another aspect of the present application, the present invention provides process for preparing Fingolimod hydrochloride crystalline Form-α comprising the steps of—
  a. Combining the Fingolimod hydrochloride with an organic acid
  b. Optionally heating up to about 40-50° C.
  c. cooling the solution up to about 0-5° C.
  d. isolating the crystalline Form-α

In yet another aspect of the present application, the present invention provides Fingolimod hydrochloride crystalline Form-β characterized by X-ray powder diffraction pattern comprising
at least 4 characteristic 2θ° peaks selected from the XRPD peak set of 3.54, 7.07, 10.66, 15.35,
20.52, 21.43 and 25.10±0.1 2θ°. The said crystalline Form-β is further characterized by DSC
isotherm comprising at least three endothermic peaks ranging between—
  a. Peak-1—Between 40 to 45° C.
  b. Peak-2—Between 65 to 70° C.
  c. Peak-3—Between 107 to 115° C.
  d. Peak-4—Between 265 to 270° C.

In further another aspect of the present application, the present invention provides process for
preparing Fingolimod hydrochloride crystalline Form-β comprising the steps of—
  a. Combining the Fingolimod hydrochloride with organic solvent selected from dimethylformamide, dimethylacetamide, tetrahydrofuran, 2-methoxyethanol
  b. Optionally heating up to about 40-50° C. followed by cooling
  c. isolating the crystalline Form-β using another co-solvent by recrystallization In yet another aspect of the present application, the present invention provides Fingolimod Hydrochloride crystalline Form-μ characterized by X-ray powder diffraction pattern comprising at least 4 characteristic 2θ° peaks selected from the XRPD peak set of 3.54, 8.65, 10.64, 12.49, 19.45, 21.38 and 24.05±0.1 2θ°.

In yet further another aspect of the present application, the present invention provides process
for preparing Fingolimod hydrochloride crystalline Form-μ comprising the steps of—
  a. Raising the Fingolimod hydrochloride temperature up to at least melting point but less than 130° C.
  b. Cooling the melt liquid
  c. isolating the crystalline Form-μ

In further aspect, the Crystalline Forms-α, β and μ of Fingolimod HCl obtained by the processes of the present application may be formulated as solid compositions for oral administration in the form of capsules, tablets, pills, powders or granules useful in the treatment or prevention of autoimmune related disorder including multiple sclerosis.

DETAILED DESCRIPTION

As set forth herein, aspects of the present invention provides crystalline polymorphic forms α, β and μ of Fingolimod HCl (I) and processes for preparation thereof.

Individual embodiments of the present invention are detailed herein below separately.

In one embodiment of the present application, it provides Fingolimod hydrochloride crystalline Form-α characterized by X-ray powder diffraction pattern comprising at least 5 characteristic 2θ° peaks selected from the XRPD peak set of 10.51, 15.20, 19.27, 21.77, 23.12, 24.91, 26.14, 26.46, 29.03, 33.47 and 35.46±0.1 2θ°. The said crystalline Form-α may be further characterized by DSC isotherm comprising at least three endothermic peaks ranging between—
a. Peak-1—Between 40 to 43° C.
b. Peak-2—Between 65 to 68° C.
c. Peak-3—Between 105 to 110° C.
d. Peak-4—Between 270 to 280° C.

Figure 1:
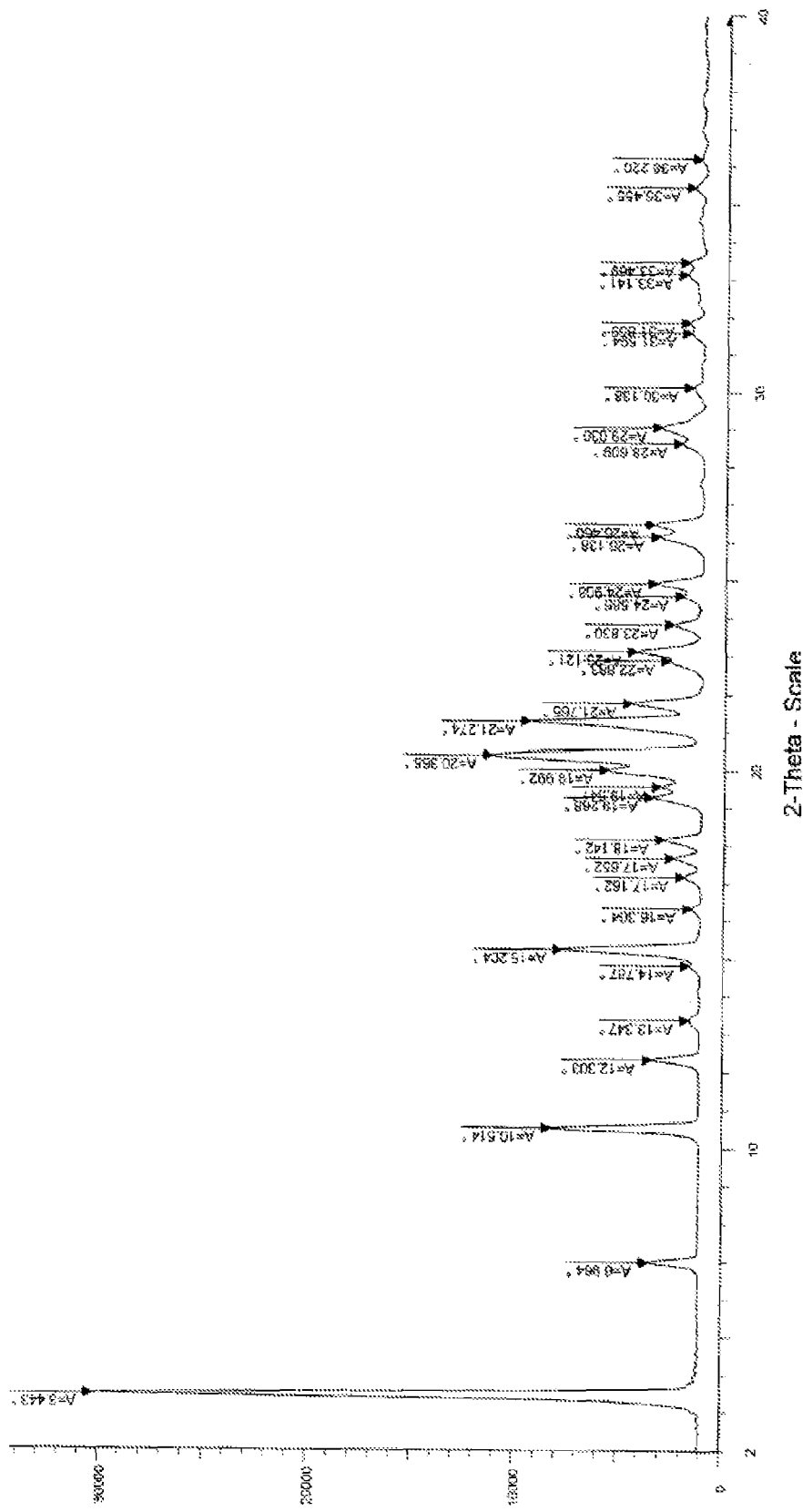
FIG. 1 is an Illustration of an X-ray powder diffraction (XRPD) pattern of Fingolimod hydrochloride-Form α, prepared according to Example-1

Fingolimod hydrochloride crystalline Form-α characterized by X-ray powder diffraction pattern comprising at least 5 characteristic 2θ° peaks selected from the XRPD peak set of 10.51, 15.20, 19.27, 21.77, 23.12, 24.91, 26.14, 26.46, 29.03, 33.47 and 35.46±0.1 2θ° is having X-ray powder diffraction pattern substantially according to FIG. 1 and DSC isotherm comprising the endothermic peaks ranging between 40 to 43° C. (Peak-1), 65 to 68° C. (Peak-2), 105 to 110° C. (Peak-3) and/or 270 to 280° C. (Peak-4) is having DSC isothermal pattern substantially according to FIG. 2.

The characteristic peaks and their d spacing values of the new crystalline Form-α are tabulated in the Table-1.

TABLE 1

Characteristic XRPD Peaks of Crystalline Form-α

| S. No. | Angle (2θ°) | d Spacing Value (A°) |
|---|---|---|
| 1. | 10.51 | 8.407 |
| 2. | 15.20 | 5.823 |
| 3. | 19.27 | 4.602 |
| 4. | 21.77 | 4.080 |
| 5. | 23.12 | 3.844 |

TABLE 1-continued

Characteristic XRPD Peaks of Crystalline Form-α

| S. No. | Angle (2θ°) | d Spacing Value (A°) |
|---|---|---|
| 6. | 24.91 | 3.572 |
| 7. | 26.14 | 3.407 |
| 8. | 26.46 | 3.366 |
| 9. | 29.03 | 3.073 |
| 10. | 33.47 | 2.675 |
| 11. | 35.46 | 2.530 |

In another embodiment of the present invention, it provides process for preparing Fingolimod hydrochloride crystalline Form-α characterized by X-ray powder diffraction pattern comprising at least 5 characteristic 2θ° peaks selected from the XRPD peak set of 10.51, 15.20, 19.27, 21.77, 23.12, 24.91, 26.14, 26.46, 29.03, 33.47 and 35.46±0.1 2θ° and DSC isotherm comprising the endothermic peaks ranging between 40 to 43° C. (Peak-1), 65 to 68° C. (Peak-2), 105 to 110° C. (Peak-3) and/or 270 to 280° C. (Peak-4) comprising the steps of—
a. Combining the Fingolimod hydrochloride with an organic acid
b. Optionally heating up to about 40-50° C.
c. cooling the solution up to about 0-5° C.
d. isolating the crystalline Form-α

Combining the Fingolimod hydrochloride with as Organic acid comprise either mixing or suspending or making solution with organic acids, selected from C1 to C4 carboxylic acid. In one of the particular embodiment, acetic acid is used as an organic acid for making Form-α. The combining of an organic acid may be carried out at ambient temperature; however temperature may be raised to any temperature up to below 50° C., if desired.

Any form of Crude or Pure Fingolimod Hydrochloride obtained by known processes can be used for preparing Form-α.

The combined mixture may be maintained for about 1-2 hrs, however, this time may be more, but, depending upon achieving the clear solution and equilibration to impurity profile compliance.

The process related impurities, including unreacted intermediates, side products, degradation products and other medium dependent impurities, that appears in the impurity profile of the Fingolimod hydrochloride can substantially removed by the process of the present invention resulting in the formation crystalline form-α. A substantially pure product having purities more than 99% (by HPLC) can be obtained by the process of the present invention. In view of maintaining the equilibrium to the impurity profile compliance, the process requires quality checks, while raising the temperature, wherever required up to 50° C.

Reaction mass can be cooled up to 25-30° C. and subjected to stir for about 1-2 hrs. Further cooling the reaction mass ranging between 0-10° C. followed by stirring for about 1-2 hours may also carried out. The product may be isolated from the reaction mass by conventional processes including filtering and optional drying, which may be carried out at room temperature for the suitable durations to retain the crystalline polymorphic form characteristics.

In yet another embodiment of the present application, it provides Fingolimod hydrochloride crystalline Form-β characterized by X-ray powder diffraction pattern comprising at least 4 characteristic 2θ° peaks selected from the XRPD peak set of 3.54, 7.07, 10.66, 15.35, 20.52, 21.43 and 25.10±0.1

2θ°. The said crystalline Form-β may be further characterized by DSC isotherm comprising at least three endothermic peaks ranging between—
 a. Peak-1—Between 40 to 45° C.
 b. Peak-2—Between 65 to 70° C.
 c. Peak-3—Between 107 to 115° C.
 d. Peak-4—Between 265 to 270° C.

Figure 3:
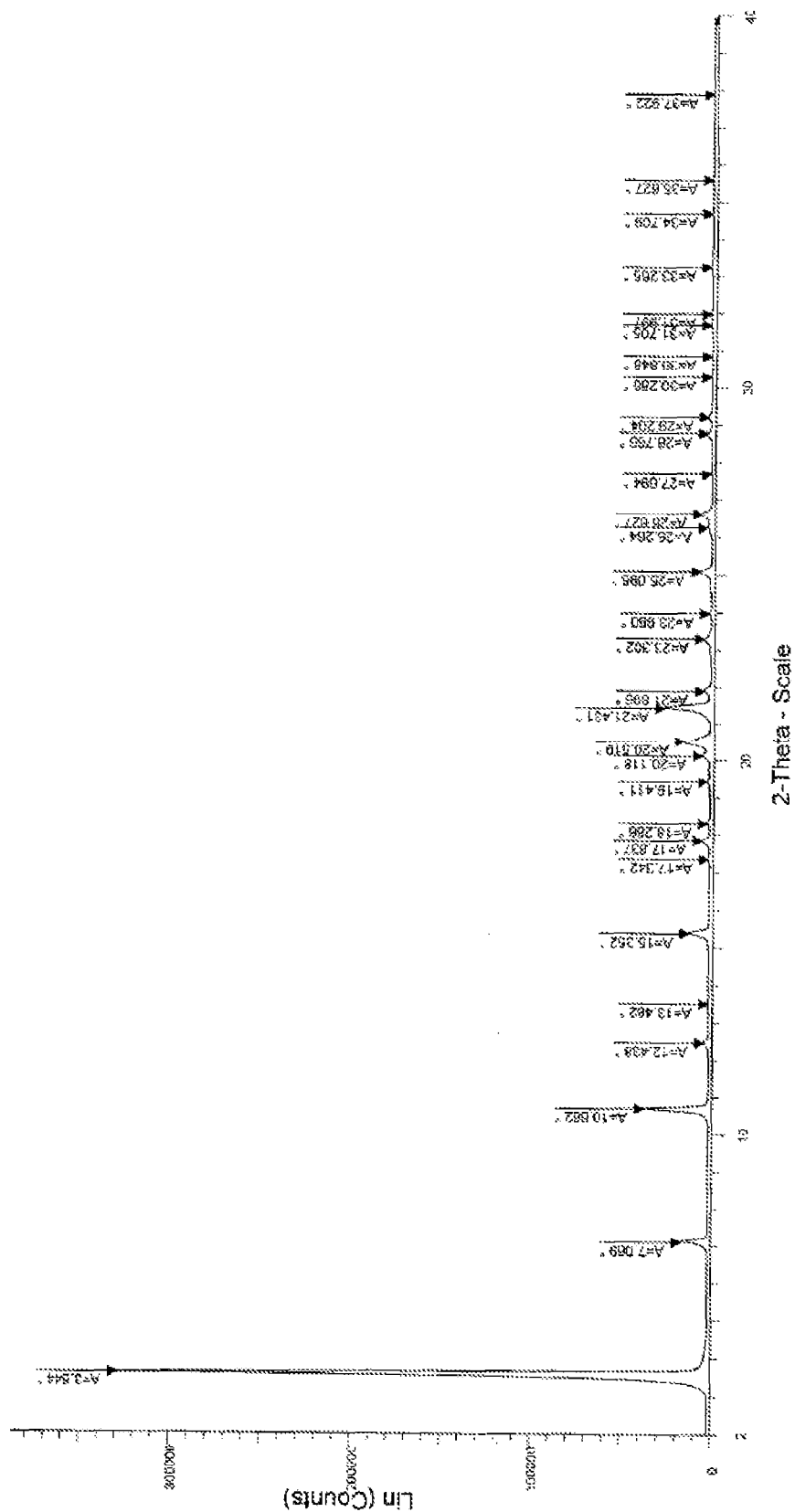
FIG. 3 is an Illustration of an X-ray powder diffraction (XRPD) pattern of Fingolimod hydrochloride-Form β, prepared according to Example-2 Process-A

Fingolimod hydrochloride crystalline Form-β characterized by X-ray powder diffraction pattern comprising at least 4 characteristic 2θ° peaks selected from the XRPD peak set of 3.54, 7.07, 10.66, 15.35, 20.52, 21.43 and 25.10±0.1 2θ° is having X-ray powder diffraction pattern substantially according to FIG. 3 and DSC isotherm comprising the endothermic peaks ranging between 40 to 45° C. (Peak-1), 65 to 70° C. (Peak-2), 107 to 115° C. (Peak-3) and/or 265 to 270° C. (Peak-4) is having DSC isothermal pattern substantially according to FIG. 4.

The characteristic peaks and their d spacing values of the new crystalline Form-β are tabulated in the Table-2.

TABLE 2

Characteristic XRPD Peaks of Crystalline Form-β

| S. No. | Angle (2θ°) | d Spacing Value (A°) |
|---|---|---|
| 1. | 3.54 | 24.908 |
| 2. | 7.07 | 12.494 |
| 3. | 10.66 | 8.290 |
| 4. | 15.35 | 5.767 |
| 5. | 20.52 | 4.325 |
| 6. | 21.43 | 4.143 |
| 7. | 25.10 | 3.546 |

In another embodiment of the present invention, it provides process for preparing Fingolimod hydrochloride crystalline Form-β characterized by X-ray powder diffraction pattern comprising at least 4 characteristic 2θ° peaks selected from the XRPD peak set of 3.54, 7.07, 10.66, 15.35, 20.52, 21.43 and 25.10±0.1 2θ° and DSC isotherm comprising the endothermic peaks ranging between 40 to 45° C. (Peak-1), 65 to 70° C. (Peak-2), 107 to 115° C. (Peak-3) and/or 265 to 270° C. (Peak-4) comprising the steps of—
 a. Combining the Fingolimod hydrochloride with organic solvent selected from dimethylformamide, dimethylacetamide, tetrahydrofuran, 2-methoxyethanol
 b. Optionally heating up to about 40-50° C. followed by cooling
 c. isolating the crystalline Form-β using another co-solvent by recrystallization Combining the Fingolimod hydrochloride with as Organic solvents for preparing Form-β comprise either mixing or suspending or making solution with organic solvent selected from dimethylformamide, dimethylacetamide, tetrahydrofuran, 2-methoxyethanol. In one of the particular embodiment, dimethylformamade is used as an organic solvent for making Form-β. The combining of an organic solvent may be carried out at ambient temperature; however temperature may be raised to any temperature up to below 50° C., whenever desired.

As mentioned earlier, any form of Crude or Pure Fingolimod Hydrochloride obtained by known processes can be used for preparing Form-β.

The combined mixture may be maintained for about 1-2 hrs, however, this time may be more, but, depending upon achieving the clear solution and equilibration to impurity profile compliance.

The process related impurities, including unreacted intermediates, side products, degradation products and other medium dependent impurities, that appears in the impurity profile of the Fingolimod hydrochloride can substantially removed by the process of the present invention resulting in the formation crystalline form-β. In view of maintaining the equilibrium to the impurity profile compliance, the process requires quality checks, while raising the temperature, whenever required up to 50° C.

Reaction mass can be cooled up to 0-30° C. and subjected to stir for about 1-2 hrs. The product may be isolated from the reaction mass by combining with co-solvent selected from ketone (C3 to C8) or nitrile (C2 to C4) or alcohol (C1 to C4), followed by conventional processes including filtering and optional drying, which may be carried out at room temperature for the suitable durations to retain the crystalline polymorphic form characteristics.

In yet another embodiment of the present application, it provides Fingolimod hydrochloride crystalline Form-μ characterized by X-ray powder diffraction pattern comprising at least 4 characteristic 2θ° peaks selected from the XRPD peak set of 3.54, 8.65, 10.64, 12.49, 19.45, 21.38 and 24.05±0.1 2θ°.

Figure 5:
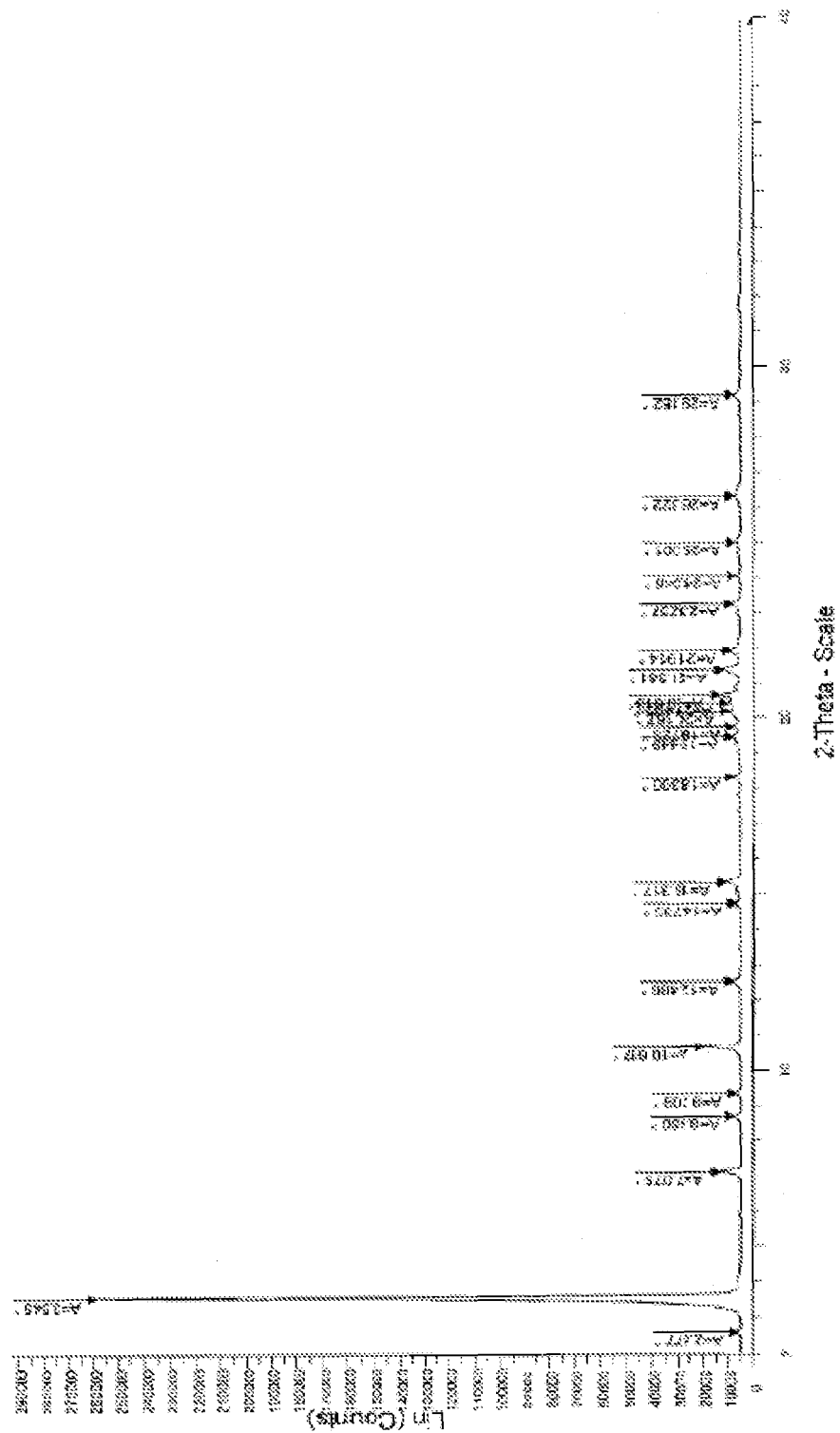
FIG. 5 is an Illustration of an X-ray powder diffraction (XRPD) pattern of Fingolimod hydrochloride-Form μ, prepared according to Example-3

Fingolimod hydrochloride crystalline Form-μ characterized by X-ray powder diffraction pattern comprising at least 4 characteristic 2θ° peaks selected from the XRPD peak set of 3.54, 8.65, 10.64, 12.49, 19.45, 21.38 and 24.05±0.1 2θ° is having X-ray powder diffraction pattern substantially according to FIG. 5.

The characteristic peaks and their d spacing values of the new crystalline Form-μ are tabulated in the Table-3.

TABLE 3

Characteristic XRPD Peaks of Crystalline Form-μ

| S. No. | Angle (2θ°) | d Spacing Value (A°) |
|---|---|---|
| 1. | 3.54 | 24.905 |
| 2. | 8.65 | 10.214 |
| 3. | 10.64 | 8.310 |
| 4. | 12.49 | 7.084 |
| 5. | 19.45 | 4.560 |
| 6. | 21.38 | 4.152 |
| 7. | 24.05 | 3.698 |

In another embodiment of the present invention, it provides process for preparing Fingolimod hydrochloride crystalline Form-μ characterized by X-ray powder diffraction pattern comprising at least 4 characteristic 2θ° peaks selected from the XRPD peak set of 3.54, 8.65, 10.64, 12.49, 19.45, 21.38 and 24.05±0.1 2θ° comprising the steps of—
 a. Raising the Fingolimod hydrochloride temperature up to at least melting point but less than 130° C.
 b. Cooling the melt liquid
 c. isolating the crystalline Form-μ.

Any form of Crude or Pure Fingolimod Hydrochloride obtained by known processes can be used for preparing Form-μ. The rise in temperature for the preparing melt of the Fingolimod Hydrochloride can be slow in order to provide consistency and uniformity of the melt liquid phase. In a particular embodiment, melt temperature attained was 120-125° C.

Simultaneously, it is essentially required to cool the melt in the successive lower rate of cooling in order to retain the characteristics of Form-μ.

Crystalline Form-μ can be isolated by conventional processes, which are not limited to scrapping, breaking, triturating and if required conventional drying.

In further aspect, the Crystalline Forms-α, β and μ of Fingolimod HCl obtained by the processes of the present application may be formulated as solid compositions for oral administration in the form of capsules, tablets, pills, powders or granules useful in the treatment or prevention of autoimmune related disorder including multiple sclerosis.

Different crystalline forms of the present invention may have one or more advantageous and desirable properties compared to the known Fingolimod Base, which are not limited to better stability, solubility and quality parameter leading to improved storage and distribution.

The Crystalline Forms-α, β and μ of Fingolimod HCl described herein may be characterized by X-ray powder diffraction pattern (XRPD) and Thermal techniques such as differential scanning calorimetric (DSC) Analysis. The samples of Fingolimod HCl Crystalline Forms-α, β and μ were analyzed by XRPD on a Bruker AXS D8 Advance Diffractometer using X-ray source-Cu Kα radiation using the wavelength 1.5418 Å, however, DSC analysis were carried out on a Perkin Elmer Pyris 7.0 instrument. Illustrative examples of analytical data for the crystalline solids 'Form-α, β and μ' obtained in the Examples are set forth in the FIGS. 1-5.

In another embodiment, the Crystalline Forms-α, β and μ of Fingolimod HCl obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Forms-α, β and μ of Fingolimod HCl of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Crystalline Forms-α, β and μ of Fingolimod HCl of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXAMPLE 1

Preparation of Crystalline Fingolimod Hydrochloride (Form-α)

Charge 10 ml acetic acid at ambient temperature followed by slow addition of 1.0 gm of Crude or Pure Fingolimod Hydrochloride obtained from any source in round bottom flask under continued stirred. Raise the temperature up to about 40-50° C. and maintained for about 1-2 hrs. (This time may be more, however, depending upon achieving the clear solution and equilibration to impurity profile compliance). Cool the reaction mass up to 25-30° C. and stir for about 1-2 hrs at 25-30° C. Further, cool the reaction mass up to 0-5° C. and stir for about 2 hrs. Filter the reaction mass and isolating the crystalline product after 12 hours of drying at room temperature.

Yield 0.36 gm

Figure 2:
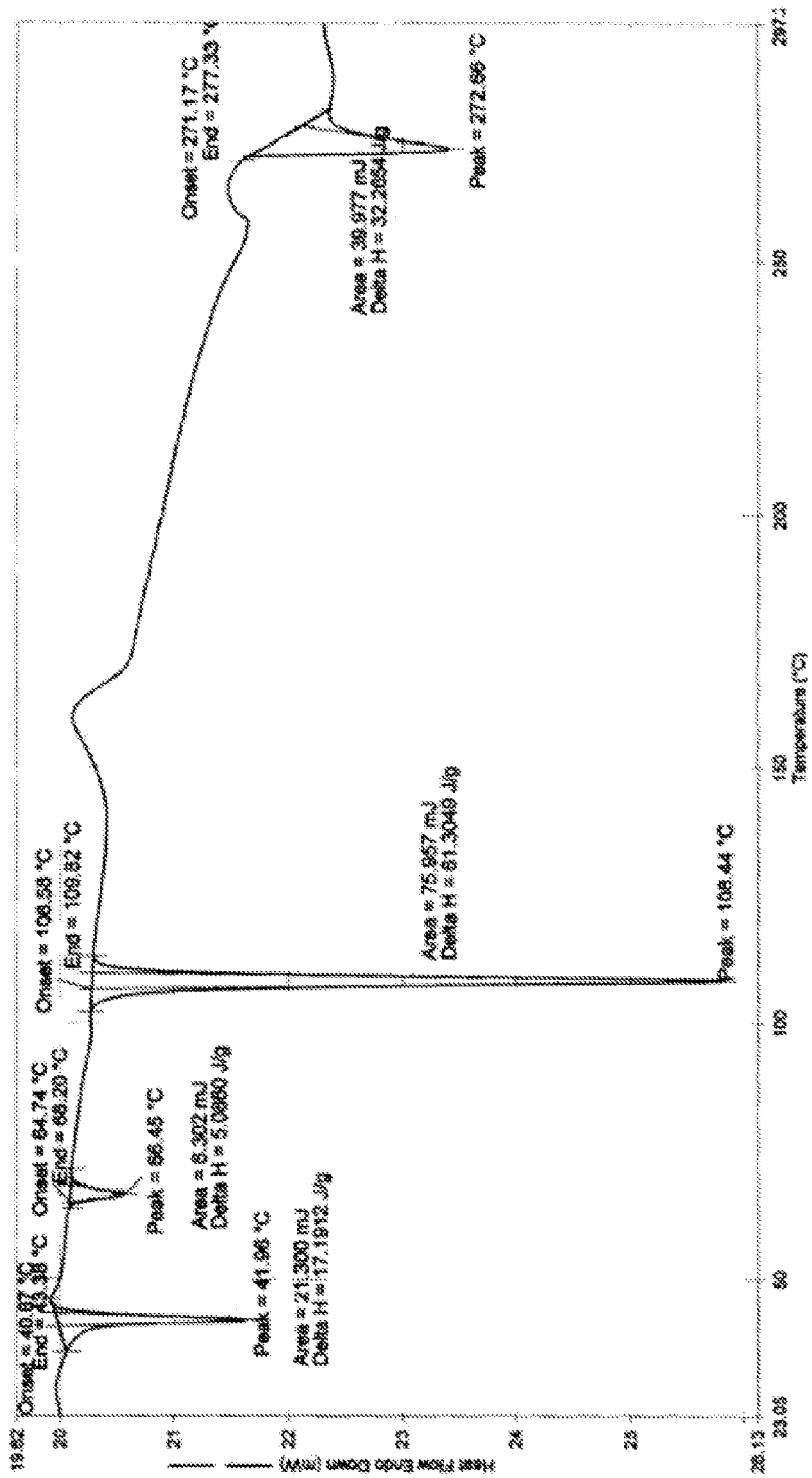
FIG. 2 is an Illustration of a differential scanning calorimetric ("DSC") curve of Fingolimod hydrochloride, prepared according to Example-1

XRPD as per FIG. 1; and DSC as per FIG. 2

EXAMPLE 2

Preparation of Crystalline Fingolimod Hydrochloride (Form-β)

Process-A:

Charge 3 ml DMF at ambient temperature followed by slow addition of 2.0 gm of Crude or Pure Fingolimod Hydrochloride obtained from any source in round bottom flask under continued stirred. Stirr and maintain the solution for 15-30 minutes to ensure clear solution. Slowly add 30.0 ml acetone at ambient temperature in about 1 hour time. Cool the reaction mass up to 0-5° C. and stir for about 2 hrs. Filter the reaction mass and isolating the crystalline product after 12 hours of under vacuum drying at room temperature.

Yield 1.37 gm

Figure 4:
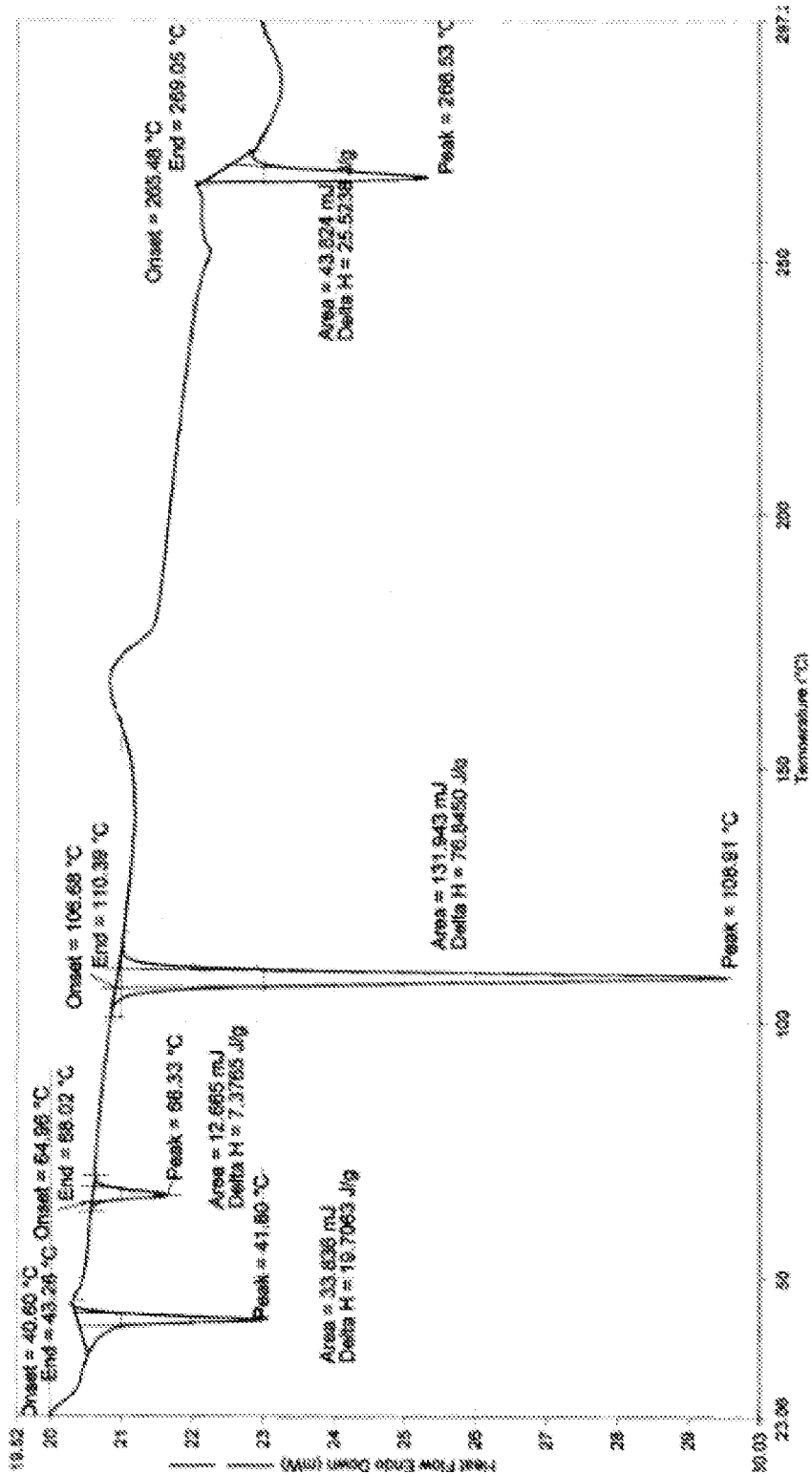
FIG. 4 is an Illustration of a differential scanning calorimetric ("DSC") curve of Fingolimod hydrochloride, prepared according to Example-2 Process-A

XRPD as per FIG. 3; and DSC as per FIG. 4

Process-B:

Charge 3 ml THF at ambient temperature followed by slow addition of 2.0 gm of Crude or Pure Fingolimod Hydrochloride obtained from any source in round bottom flask under continued stirred. Stir and maintain the solution for 10-20 minutes to ensure clear solution. Slowly add 60.0 ml acetone at ambient temperature in about 1 hour time. Cool the reaction mass up to 0-5° C. and stir for about 2 hrs. Filter the reaction mass and isolating the crystalline product after 12 hours of under vacuum drying at about 45° C.

Yield 1.51 gm

Process-C:

Charge 5 ml 2-Methoxy ethanol at ambient temperature followed by slow addition of 2.0 gm of Crude or Pure Fingolimod Hydrochloride obtained from any source in round bottom flask under continued stirred. Stir and maintain the solution for 10-15 minutes to ensure clear solution. Slowly add 60.0 ml Acetonitrile at room temperature in about 1 hour time. Stir for about 2 hours at room temperature. Cool the reaction mass up to 0-5° C. and maintained the stirring for about 2 hrs. Filter the reaction mass and isolating the crystalline product after 12 hours of under vacuum drying at about 20-25° C.

Yield –1.89 gm

EXAMPLE 3

Preparation of Crystalline Fingolimod Hydrochloride (Form-µ)

Charge 1.0 gm of Crude or Pure Fingolimod Hydrochloride obtained from any source in round bottom flask. Raise the temperature slowly till 120-125° C. Once the melt is formed and the clear melt becomes visible, cool the melted mass slowly up to 20-25° C. (RT) in about 2 hours time. Scrap the crystalline material as Form-µ.

Yield –0.89 gm

XRPD as per FIG. 5

We claim:

1. Fingolimod hydrochloride crystalline Form-β characterized by X-ray powder diffraction pattern comprising characteristic 2θ° peaks selected from the XRPD peak set of 3.54, 7.07, 10.66, 15.35, 20.52, 21.43 and 25.10±0.1 2θ°.

2. Fingolimod hydrochloride crystalline Form-β according to claim 1, which is further characterized by DSC isotherm comprising endothermic peaks ranging between—
   a. Peak-1—Between 40 to 45° C.
   b. Peak-2—Between 65 to 70° C.
   c. Peak-3—Between 107 to 115° C.
   d. Peak-4—Between 265 to 270° C.

3. Fingolimod hydrochloride crystalline Form-β characterized by X-ray powder diffraction pattern comprising characteristic 2θ° peaks selected from the XRPD peak set of 3.54, 7.07, 10.66, 15.35, 20.52, 21.43 and 25.10±0.1 2θ° and DSC isotherm comprising the endothermic peaks ranging between 40 to 45° C. (Peak-1), 65 to 70° C. (Peak-2), 107 to 115° C. (Peak-3) and/or 265 to 270° C. (Peak-4).

4. Fingolimod hydrochloride crystalline Form-β according to claim 3, characterized by X-ray powder diffraction pattern as disclosed in FIG. 3 and DSC isothermal pattern as disclosed in FIG. 4.

5. A process for preparing Fingolimod hydrochloride crystalline Form-β comprising the steps of—
   a. combining the Fingolimod hydrochloride with organic solvent selected from dimethylformamide, dimethylacetamide, tetrahydrofuran and 2-methoxyethanol;
   b. optionally heating upto about 40-50° C. followed by cooling; and
   c. isolating the crystalline Form-β using another co-solvent selected from acetone or acetonitrile by recrystallization.

6. A process for preparing Fingolimod hydrochloride crystalline Form-β according to claim 5, wherein organic solvent may be selected from dimethylformamide, dimethylacetamide, tetrahydrofuran, 2-methoxyethanol and co-solvent selected from acetone or acetonitrile.

* * * * *